United States Patent [19]

Mamuzic et al.

[11] Patent Number: 4,835,322

[45] Date of Patent: May 30, 1989

[54] PROCESS FOR PRODUCING 4,4′-DIBROMODIPHENYL ETHER

[75] Inventors: Rastko I. Mamuzic, West Lafayette; Bhabatosh Bhattacharya, Lafayette, both of Ind.

[73] Assignee: Great Lakes Chemical Corporation, West Lafayette, Ind.

[21] Appl. No.: 110,154

[22] Filed: Oct. 19, 1987

[51] Int. Cl.$^4$ .............................................. C07C 41/12
[52] U.S. Cl. .................................................... 568/639
[58] Field of Search ......................................... 568/639

[56] References Cited

U.S. PATENT DOCUMENTS

| | | | |
|---|---|---|---|
| 2,022,634 | 11/1935 | Britton et al. | 260/150 |
| 3,192,272 | 6/1965 | Asadorian | 260/650 |
| 3,285,965 | 11/1966 | Jenkner | 260/612 |
| 3,366,694 | 1/1968 | Thompson | 260/612 |
| 3,518,316 | 6/1970 | Cumbo | 568/639 |
| 3,752,856 | 8/1973 | Nagy et al. | 568/639 |
| 3,793,377 | 2/1974 | Hennis | 568/639 |
| 3,965,197 | 6/1976 | Stepniczka | 260/623 H |
| 4,214,103 | 7/1980 | Garman et al. | 568/639 |

FOREIGN PATENT DOCUMENTS

| | | |
|---|---|---|
| 1930594 | 1/1970 | Fed. Rep. of Germany . |
| 2242519 | 3/1984 | Fed. Rep. of Germany . |
| 1029874 | 5/1966 | United Kingdom . |
| 1411524 | 10/1975 | United Kingdom . |
| 1436657 | 5/1976 | United Kingdom . |
| 1472383 | 5/1977 | United Kingdom . |

OTHER PUBLICATIONS

Bakhvalov et al., *Chemical Abstracts*, vol. 70, No. 106118e (1969).
Nilsson et al., *Chemical Abstracts*, vol. 88, No. 22273k (1978).
Bakhvalov et al., *Chemical Abstracts*, vol. 72, No. 110930x (1970).
Akchurin *Chemical Abstracts*, vol. 40, No. 557 (1946).
Engelsma et al., *Rec. Tran. Chim. Pays-Bas*, vol. 80, pp. 526-532 (1961).
Org. Syntheses, Coll., vol. IV, pp. 256-258.

*Primary Examiner*—Bruce D. Gray

[57] ABSTRACT

4,4′-dibromodiphenyl ether may be obtained in high yield and purity by the uncatalyzed "neat" bromination of diphenyl oxide, followed by methanol digestion.

6 Claims, No Drawings

PROCESS FOR PRODUCING 4,4'-DIBROMODIPHENYL ETHER

BACKGROUND OF THE INVENTION

Field of the Invention

The present invention relates to a process for producing 4,4'-dibromodiphenyl ether and, more particularly, to the uncatalyzed "neat" bromination of diphenyl ether followed by a subsequent digestion with methanol to produce 4,4'-dibromodiphenyl ether in very high yield and purity.

Description of the Prior Art

A number of historical approaches have been used in producing 4,4'-dibromodiphenyl ether. Thus, the product was first produced by brominating diphenyl ether in solution in carbon disulfide (Hoffmeister, Ann. 159, 210). Subsequent approaches involved bromination of diphenyl ether in carbon tetra-chloride or carbon disulfide in the presence of iodine (Mailhe, Murat, Comp.rend. 154, 603; Bl.[4] 11, 332); diazotizing of 4'-bromo-4-amino diphenyl ether, conversion to diazonium perbromide, and subsequent decomposition of the latter with hot acetic acid (La Fevre, et al. Soc. 1927, 1171). A later approach involved treatment of diphenyl ether with bromine in glacial acetic acid in the presence of $CuCO_3$ (Akchurin, C. A., 1946, 557); by heating the sodium salt of 4-(4-bromophenoxy)-benzene sulfonic acid with bromine in water at 50° C. (Suter, Am. Soc. 53 (1931) 1112, 1114); and by heating of 4-(4-bromophenoxy)-phenyl phosphonic acid with bromine in water at 160° C. (Davies, et al. Soc. 1932, 2880, 2881).

It has been suggested that bromination of diphenyl ether without catalysts produces a mixture containing 56-59 percent unreacted diphenyl ether, 36-40 percent monobromodiphenyl ether, and 3-6 mole percent of dibromo derivatives of diphenyl ether. The monobromo fraction contained 95-98 percent para-bromodiphenyl ether and 2-5 percent ortho-bromodiphenyl ether (Bakhvalov, O. V., et al., Zh. Org. Khim 1969, 5(2), 331-336; C.A. 70: 106118e);

German Offen. No. 1,930,594 describes the preparation of 4,4'-dibromodiphenyl ether in 90 percent yield by brominating diphenyl ether in liquid sulfur dioxide as a reaction medium at a temperature below 0° C.

Still other approaches to the preparation of 4,4'-dibromodiphenyl ether involve condensation reactions. Thus, when bromobenzenes were heated with iodyl sulfate and then with concentrated, hydrochloric acid, $R_2I^+Cl^-$ was formed which, on coupling with para-bromophenol in aqueous solution containing sodium hydroxide, gave 4,4'-dibromodiphenyl ether. (Nilsson, C. A., et al., Chemosphere 1977, 6(9), 599-607; C.A. 88: 22273k). Another low yield synthesis of 4,4'-dibromodiphenyl ether utilizes coupling of para-dibromobenzene with phenol. Thus, heating para-dibromobenzene with phenol and potassium hydroxide in the presence of freshly precipitated copper at 180° C. with continuous water removal gave 27 percent yield of para-dibromo diphenyl ether, with somewhat higher yields being obtained at higher temperature. (Bakhvalov, et al., Izv. Akad Nauk SSSR, Ser.Khim. 1970, (1), 143-5;, C.A. 72: 110930x). German Offen No. 2,242,519 describes the synthesis of 4,4'-dibromodiphenyl ether by a soventless Ullmann reaction of halobenzenes with alkali metal phenolates in the presence of cuprous or cupric oxide at 130°-65° C.

None of the foregoing preparations for 4,4'-dibromodiphenyl ether permit the desired production of 4,4'-dibromodiphenyl ether in very high isomer purity and yield.

Bromination of biphenyl with bromine vapor carried out in a vacuum dessicator gives 4,4'-dibromobiphenyl in 75-77 percent yield after recrystallization (Org.Syntheses, Coll. Vol. IV, pp. 256-258). However, the bromination of diphenyl is not readily comparable to bromination of diphenyl ether because of inconsistent and unpredictable formation of position isomers at various bromination levels.

"Neat" bromination (i.e., bromination of a substrate using stoichiometric amounts of bromine without solvent or other reaction medium) utilizing bromination catalysts has been described for a variety of higher brominated diphenyl ethers and biphenyls. For example, U.S. Pat. No. 4,214,103 describes the catalyzed neat bromination of diphenyl ether to produce partially brominated diphenyl ethers, especially brominated diphenyl ethers of five to eight bromine atoms per molecule, containing undesirable amounts of occluded free bromine, by-product hydrogen bromide, catalyst residue and other materials which adversely affect the color of the product and which may diminish its thermal stability. British Patent No. 1,436,657 relates to a liquid phase bromination of aromatic compounds (e.g., diphenyl ether) containing two or more non-condensed benzene nuclei in the presence of a halogen carrier (e.g., iron powder or the like) using an approximately 10 percent stoichiometric excess of bromine in the substantial absence of a diluent or solvent liquid to produce pentabromodiphenyl oxide.

British Patent No. 1,029,874 describes the production of tribromobiphenyl from the bromination of biphenyl with a stoichiometric amount of bromine in the presence of a bromination catalyst.

A number of other patents describe the catalyzed bromination of diphenyl oxide with or without a solvent to achieve bromination levels of 3, 4 and 6 bromine atoms or more (e.g., U.S. Pat. Nos. 3,285,965; 2,022,634: and British No. 1,472,383).

"Neat" bromination technology has been used for other materials as well in U.S. Pat. No. 3,192,272 (tribromination of dialkyl benzenes) and U.S. Pat. No. 3,366,694 (3-chloro-diphenyl ether). Various other patents describe the catalyzed perbromination of diphenyl ether under varying reaction conditions in the absence of a solvent or other diluent (e.g., U.S. Pat. Nos. 3,752,856; and 3,965,197; and British Patent Spec No. 1,411,524).

None of the foregoing prior art teaches the utilization of neat bromination technology to produce high yields of isomer specific 4,4'-dibromodiphenyl ether without catalysts, solvents and other reaction diluents.

Accordingly, the primary object of the present invention is to provide a new process for producing 4,4'-dibromodiphenyl ether.

A related object is the provision of a unit process for producing higher purity 4,4'-dibromodiphenyl ether in high yield and assay.

A still further object is the provision of a process of the character described which avoids the disadvantages of the various prior art techniques for producing 4,4'-dibromodiphenyl ether.

SUMMARY OF THE INVENTION

The foregoing and other objects, advantages and features of the present invention may be achieved by the uncatalyzed neat bromination of diphenyl ether and subsequent purification of the reaction product by digestion with methanol.

More particularly, the process involves reacting a slight stoichiometric excess of bromine with diphenyl oxide in the substantial absence of a bromination catalyst and solvent or other diluent, while maintaining the temperature at a level sufficient to maintain the reaction mixture in a liquid state. Thereafter, unreacted bromine is removed from the reaction mixture, which is then digested with methanol. The purified 4,4'-dibromodiphenyl ether is then recovered in high yield and assay.

DETAILED DESCRIPTION OF THE PREFERRED EMBODIMENTS

The present invention utilizes "neat" bromination technology to produce of a highly specific isomer of dibromodiphenyl ether, namely, 4,4'-dibromodiphenyl ether, in very high yield and purity. Among the significant novel aspects of the present invention is the uncatalyzed reaction step of brominating diphenyl ether "neat," that is, adding bromine gradually to diphenyl ether without using solvents or other diluents, at a gradually increasing temperature. A slight (e.g., desirably about 4 percent, and preferably no more than about 10 percent) excess of bromine is utilized. Substantially any suitable excess may be employed, but excesses of more than 10 percent are generally undesirable. The reaction mixture is preferably agitated during the bromination step.

Carrying out the bromination "neat" insures the highest possible reactor productivity since the reaction vessel contains only the diphenyl ether substrate at the outset and only the desired brominated reaction product at completion. Carrying out the reaction in the absence of catalysts is also advantageous in that separation of catalyst residues from the crude reaction product is not required as is the case in the prior art catalyzed processes.

A further novel aspect of the invention involves carrying out the bromination reaction at gradually increasing reaction temperature. Bromine addition normally begins at approximately room temperature. Lower or higher bromination initiation temperatures could be used but would require the expenditure of energy. The use of ambient conditions to initiate the reaction is, therefore, preferred.

The temperature of the reaction mixture is gradually increased throughout bromine addition by application of heat finishing at approximately 60° C. Utilization of this reaction temperature profile insures that the reaction mixture remains liquid throughout the bromination step, while insuring that the reaction proceeds at the lowest possible temperature. Surprisingly, carrying out the bromination reaction at the lowest temperature necessary to maintain a liquid reaction medium involves the mildest possible conditions and is believed to have a beneficial effect in the production of the desired 4,4'-dibromo isomer, insuring that, at most, only traces of other undesired isomers (e.g., 2,4'-dibromodiphenyl ether) are obtained.

Following the conclusion of bromine addition, the reaction mixture is desirably agitated at elevated temperature (e.g., about 60° C.) until HBr evolution substantially stops. Air or other unreactive gas is then passed over the surface of the reaction mixture (or through it), while gradually increasing the temperature of the reaction mixture from about 60°–70° C., in order to remove excess bromine from the reaction product.

Following the neat bromination step, the crude reaction product is purified using a methanol digestion procedure. Methanol is added to the reaction product as a purification agent, and the resulting methanol suspension is agitated at reflux temperature and thereafter cooled to room temperature. The purified product is recovered by filtration. The product filter cake may be washed with a small additional quantity of methanol and is dried to provide a white, free-flowing crystalline solid melting at 60°–62° C. and having a 99+ percent vapor phase chromatography ("VPC") assay for 4,4'-dibromodiphenyl ether.

The amount of methanol utilized is desirably kept to a minimum in order to reduce product losses. In general, no more than about 2 parts methanol by weight is used per part by weight 4,4'-dibromodiphenyl ether product. Preferably, no more than about 2 parts methanol per 3 parts product are used. The digestion procedure may be carried out with greater relative amounts of methanol, although product yield suffers.

Use of methanol for purification of the 4,4'-dibromodiphenyl ether reaction product has several important advantages. Because methanol has a boiling point of 64.6°–65° C., it boils at a temperature close to the temperature of the finished reaction mixture (about 60° C.). Moreover, methanol is a very good purification solvent because it readily dissolves and maintains in solution undesired reaction by-products while, at the same time dissolving only very small quantities of the 4,4'-dibromodiphenyl ether product. Thus, purification is achieved without appreciably reducing yield. An added advantage of methanol is that it neutralizes the product by chemically reacting with any residual unreacted bromine and/or by-product HBr, thus eliminating the need for aqueous washes.

The methanol is also efficient since only a relatively small quantity of methanol is needed to achieve the desired level of product purification, and the methanol can be recovered by simple flash distillation from the combined process and washing mother liquors and then may be recycled. While some of the foregoing advantages may be achieved by other purification agents, only methanol permits all of these objectives to be achieved.

The product, 4,4'-dibromodiphenyl ether, a flame retardant agent useful in a variety of potential applications (e.g. polyesters and polystyrene) has also been used as a processing aid in polycarbonates. The material is also useful as a reactant for producing other di-functional 4,4 prime diphenyl ether derivatives such as 4,4 prime dihydroxydiphenyl ether.

The process of the present invention is illustrated in the following example.

EXAMPLE

Diphenyl ether (680.8, 4.0 moles) was charged to a three liter, three neck reaction flask equipped with mechanical stirrer, thermometer, dropping funnel, water-cooled reflux condenser. Bromine (1329.5 g, 8.32 moles) was charged to the dropping funnel. The agitator was turned on, and bromine addition began at ambient temperature (about 25° C.). Bromine was added drop-wise at a rate of 15 milliliters/10 minutes over a period of four hours and 50 minutes. During this period, the water bath temperature was gradually raised at the rate of 1° C./10 minutes until 60° C. was reached after six hours. The reaction mixture was agitated at 60° C. until HBr evolution substantially ceased (an additional 0.5-1 hours). Air was passed over the surface of the reaction mixture for one hour while gradually increasing the water bath temperature from 60°-70° C. in order to remove residual bromine and/or HBr.

The product was isolated and purified by adding methanol (886 g) to form a suspension, and the resulting suspension was agitated at reflux (about 65° C.) for one hour and was then allowed to cool to 25° C. with agitation.

The ambient temperature methanol suspension was filtered with suction through a sintered glass funnel, and the product cake was washed on the funnel with 197 g methanol and was allowed to dry in the air. Dibromodiphenyl ether (1208.5 g), corresponding to a yield of 92.1 percent on diphenyl ether, was obtained. The product had the following properties:
Appearance: white, crystalline solid.
Melting point: 60°-62° C.
Br (calculated 48.7 percent): 47.4 percent
VPC assay: 99.4 percent 4,4'-dibromodiphenyl ether.
The product also contains 0.4 percent of an unidentified impurity believed to be 2,4'-dibromodiphenyl ether.

Utilization of the foregoing process permits high yield and high assay of 4,4'-dibromodiphenyl ether to be obtained economically utilizing simplified reaction equipment, and without using catalyst, solvents, diluents or other expensive purification reagents.

We claim:

1. A process for preparing 4,4'-dibromodiphenyl ether comprising the steps of:
    reacting an excess of bromine with diphenyl oxide in the absence of a bromination catalyst and solvent or other diluents at a temperature sufficient to maintain the reaction mixture in a liquid state;
    removing unreacted bromine and/or by-product hydrogen bromide from the reaction mixture;
    digesting the remaining reaction mixture with methanol in sufficient amounts and at such temperature to dissolve impurities; and
    recovering the 4,4'-dibromidiphenyl ether in high yield and assay.

2. A process, as claimed in claim 1, wherein the bromine is added to the diphenyl ether and after bromine addition is completed, the reaction mixture is maintained at elevated temperature until the evolution of HBr substantially ceases.

3. A process, as claimed in claim 1, wherein the reaction is initiated at ambient temperature and the temperature of the reaction mixture is increased to about 60° C. throughout the period of bromine addition.

4. A process, as claimed in claim 1, wherein no more than about 2 parts methanol is employed per part 4,4'-dibromodiphenyl ether by weight.

5. A process as claimed in claim 1, wherein the 4,4'-dibromodiphenyl ether is recovered from the methanol by filtration at ambient temperature.

6. A process, as claimed in claim 1, wherein the excess of bromine does not exceed about 10 percent.

* * * * *

UNITED STATES PATENT AND TRADEMARK OFFICE
CERTIFICATE OF CORRECTION

PATENT NO. : 4,835,322

DATED : May 30, 1989

INVENTOR(S) : Mamuzic et al

It is certified that error appears in the above-identified patent and that said Letters Patent is hereby corrected as shown below:

Column 6, line 15, claim 1, delete "dibromidiphenyl" and substitute therefor --dibromodiphenyl--.

Signed and Sealed this

Third Day of April, 1990

Attest:

*Attesting Officer*

HARRY F. MANBECK, JR.

*Commissioner of Patents and Trademarks*